United States Patent [19]

Hippchen et al.

[11] 4,111,714

[45] Sep. 5, 1978

[54] PROCESS FOR OBTAINING AMINO ACIDS FROM THE RAW JUICES OF SUGAR MANUFACTURE

[75] Inventors: Hermann Hippchen, Saarbrucken; Hans-Georg Schneider; Renate Schwingeler, both of Euskirchen, all of Germany

[73] Assignee: Pfeifer & Langen, Cologne, Germany

[21] Appl. No.: 675,014

[22] Filed: Apr. 8, 1976

[30] Foreign Application Priority Data

Apr. 10, 1975 [DE] Fed. Rep. of Germany ....... 2515591
Apr. 10, 1975 [DE] Fed. Rep. of Germany ....... 2515621

[51] Int. Cl.$^2$ ........................ C13D 3/14; C07C 99/12; C07C 59/12; C07C 59/16

[52] U.S. Cl. ............................... 127/46 A; 127/46 R; 127/48; 127/50; 127/57; 260/501.11; 260/501.13; 195/11; 562/514; 562/513

[58] Field of Search ..................... 127/46 R, 46 A, 48, 127/50; 260/501.11, 527 R, 534 G; 195/11

[56] References Cited

U.S. PATENT DOCUMENTS

| | | | |
|---|---|---|---|
| 2,375,164 | 5/1945 | Bennett | 127/46 A X |
| 2,375,165 | 5/1945 | Nees | 127/46 A X |
| 2,413,844 | 1/1947 | Rawlings | 127/46 A |
| 2,462,597 | 2/1949 | Block | 127/46 A X |
| 2,503,767 | 4/1950 | Rawlings | 127/46 A |
| 2,510,980 | 6/1950 | Jacobs | 127/46 A |
| 2,712,552 | 7/1955 | Ventre | 260/527 R |
| 2,971,868 | 2/1961 | Assalini | 127/46 R |
| 2,976,189 | 3/1961 | Alston | 127/46 R X |
| 3,178,474 | 4/1965 | Fike | 260/534 G |
| 3,630,681 | 12/1971 | Arikawa | 260/534 G UX |
| 3,639,467 | 2/1972 | Nagai | 260/527 N |
| 3,734,773 | 5/1973 | Haley | 260/527 R X |

*Primary Examiner*—Sidney Marantz
*Attorney, Agent, or Firm*—Burgess, Dinklage & Sprung

[57] ABSTRACT

To recover amino acids from raw sugar juice, as obtained in beet extraction, the juice is treated with acid or with lime to coagulate impurities which are separated off. The juice may be treated before or after coagulation with a pectin-cleaving enzyme. The juice so pretreated can be directly passed through a strong cation exchanger and a weak anion exchanger whereby the amino acids are adsorbed. Switchover to a new cation exchanger is initiated when betaine flows out the column. Elution is effected, preferably with an ammonium compound, and eluate is collected, preferably each fraction being enriched in a different amino acid. The sugar juice may be concentrated and crystallized in known manner and is of comparatively high purity.

13 Claims, No Drawings

PROCESS FOR OBTAINING AMINO ACIDS FROM THE RAW JUICES OF SUGAR MANUFACTURE

BACKGROUND

The need for amino acids in nutrition, pharmacy, industry and science is increasing. Raw materials for their production are protein substances such as gelatins, casein etc., which are broken down to their building blocks by enzymatic or acid hydrolysis. The amino acid mixture thus obtained is separated into defined amino acids by known methods, using ion exchangers in conjunction with the means of classical chemistry. This "classical" production of amino acids is encumbered with the costs associated with the raw material (protein) and the cost of its hydrolytic cleavage to the amino acid mixture.

On the other hand, the sugar beet appears to be an inexhaustible and cheap but hiterto virtually unused source for the production of amino acids, because in it the amino acids are already present as such. In the diffusion process, that is, in the extraction of the sugar beet for the recovery of sugar, they pass into the raw juice without having caused any costs. The raw juice is turbid and unfiltrable due to the presence of cell debris. Furthermore, it contains colloids, proteins, pectin and saponin, which must be removed.

To the sugar technician, amino acids represent undesirable nitrogen. Upon the concentration of the sugar juices, they combine with the invert sugar naturally present in the sugar beet to form dark discolorants. Glutamine is especially undesirable: it becomes transformed to pyrrolidone carboxylic acid ammonium which loses its ammonium ion at the boiling temperatures, thereby making the juice acid. This in turn brings it about that sugar (saccharose) is transformed to invert sugar, which then again reacts with amino acids to form dark discolorants. Sugar loss, more difficult crystallization, poor sugar quality and a higher production of molasses are the undesirable consequences. The declared purpose of the main liming operation is therefore the destruction of the acid amines, such as glutamine and asparagine, and of the invert sugar naturally present in the raw juice. The amino acids, which ultimately remain intact, reappear in the molasses where they still represent some value as animal feed. Also, approximately 15% of the sugar originally contained in the raw juice will be contained in the molasses.

THE INVENTION

It is the object of the invention to produce amino acids, especially glutamine and glutamic acid, and also the valuable organic acids, from raw juices of sugar manufacture, by a method which will be simple to practice on a production scale and which not only will not reduce the yield of sugar but will even increase it in comparison to classical sugar production.

The subject matter of the invention is a process for obtaining amino acids from raw juices of sugar manufacture, which is characterized in that impurities are precipitated from the raw juice by establishing a pH of 2 to 5, or by liming or by combined liming and carbonation, and they are then separated, that the raw juice thus purified is passed through very acid ion exchangers and then through weakly basic ion exchangers, that the cation exchangers are eluted with solutions of other cations, especially ammonium ions, and that the amino acids are obtained from the amino acid-rich eluate fractions. In a preferred embodiment, the purified raw juice is passed through a plurality of acid and weakly basic ion exchangers, in an alternating manner if desired.

In another preferred variant of the process, the eluate fractions in which the individual amino acids are concentrated are recovered separately, and the individual amino acids are extracted from them. Glutamine and glutamic acid, especially, are obtained in this manner.

The composition of the raw juice will vary according to location, climate, fertilization, the variety of the sugar beet, etc. It can be assumed for the sake of simplicity that 90% of its solid substance is sugar and 10% consists of non-sugar substances. The non-sugar substances consist approximately of:

15% cations, such as potassium, magnesium, sodium and calcium,

15% betaine,

30% amino acids, of which more than 50% is glutamine,

25% acids, particularly sulfuric acid, hydrochloric acid, phosphoric acid, citric acid, oxalic acid, lactic acid, malic acid, and galacturonic acid, 15% sugar-like substances, dissolved proteins, other ionogenic substances, pectins, mucins, saponins and colloids, in small amounts in each case.

50 to 60 percent of the non-sugar substances in the raw juice are worth the effort to recover them. This amounts to only 6 to 7% with respect to the recoverable sugar, but they are of economic importance because they are worth substantially more money than the same amount of sugar in each case. In addition, isolating them makes possible an increase of about 15% in the sugar yield.

In the classical method of sugar making, the sugar is obtained by concentrating a solution greatly contaminated by non-sugars; ultimately there remains an amount that can no longer be crystallized, and this is the molasses. The concentration has to be preceded by the purification of the juice, which must be performed in order to make the concentration at all possible by destroying substances which interfere with it.

In the process of the invention, the non-sugar substances are to be removed by ion exchangers for the purpose of arriving at a pure sugar solution which will be boiled to make sugar or concentrated to fluid sugar. The juices thus need to be "cleaned up" only to such an extent as to prevent harm to the exchangers. In contrast to the classical purification of the juices, all measures, such as the main liming operation for example, are avoided which would destroy the invert sugar naturally present in the raw juice, and it is not the main object to carefully prevent the inversion of saccharose, because invert sugar, as a component of fluid sugar, is a valuable end product of the process of the invention.

The juice should be left "natural," because the individual constituents are recovered by the ion exchange process, but it should be as free as possible of colloids to prevent the ion exchange resins from becoming clogged by the treatment of the juice. It would be simplest, of course, if the raw juice could be delivered just as it comes, after filtration or screening, to the ion exchange resin. This is not possible, unfortunately, because the colloid substances precipitate on the resin and in a short time clog the exchanger bed. Fine filtration of raw juice on a technical scale has always proven to be impossible unless it is subjected to some kind of special preliminary treatment.

It is essential to the practice of the process that the juice be capable of percolation, i.e., that all substances which might clog the ion exchangers or gum them up or change them irreversibly be removed from them, and that the glutamine be left completely or almost completely intact in this preliminary treatment of the raw juice.

This preliminary treatment of the juice will be referred to hereinafter as the "mild cleaning" of the juice. It can be an acid cleaning or an alkaline cleaning.

Acid juice cleaning is known. For this purpose the raw juice is acidified to a pH of 3.0 to 4.2, so that flocculation will occur at the isoelectric point of the pectin-protein complex, which can vary according to the origin and composition of the raw juice and will be, as a rule, between pH 3.4 and 3.7. The flocculated substances suspended in the raw juice are settled out by decantation or centrifugation, since these juices are difficult to filter; in all of the known processes this did not matter because flocculation in the acid range was to be followed in all cases by an additional cleaning in the alkaline range.

In the alkalization of the juice to prevent inversion, a relatively great discoloration had always been observed as a result of the decomposition of the invert sugar already formed. The acid cleaning process did not find its way into sugar manufacture on account of the increase it produced in the invert sugar, which could not be prevented in spite of flocculation in the cold. Even when the clear juice first obtained by acid cleaning is treated with ion exchangers, the juice or the sirup obtained therefrom by concentration is not pure enough to be sold directly to the end consumer as fluid sugar or invert sirup. Evidently no one succeeded in separating protein substances and pectins completely from the sugar solution, and on the other hand it is essential to the economical production of amino acids from the raw juices of sugar manufacture that the sugar, too, be obtainable in a simple manner in the forms in which it is conventionally sold.

For the acid, mild cleaning of the juice as a step in the process of the invention, the raw juice of sugar manufacture, which has a pH of 6 as a rule, is depulped and defoamed, and adjusted to a pH of 2 to 5 with physiologically unobjectionable acids, especially those whose anions occur in the raw juice anyway, and which are produced in a later step of the process. Which pH value within this range is best for the completest possible flocculation of the colloids and the simplest possible removal thereof will depend on measures which are taken during the acidification or immediately thereafter.

The following variants of the mild acid cleaning of the juices are especially mentioned:

If raw juice is acidified to pH 3.2 to 3.3 with hydrochloric acid, for example, freed by decantation and centrifugation of the colloids thus flocculated, and the turbid, unfiltrable juice thus produced is passed directly through an acid or weakly basic pair of exchangers, the result will be an ash-free, virtually colorless and thermally stable, partially inverted sugar solution which complies perfectly with the food laws, but which does not satisfy all purchaser requirements because the concentrate, thickened to 65° Brix has a slight greenish tinge and its viscosity is greater than that of commercial fluid sugar; for the production of the amino acids this mild cleaning of the juice is quite sufficient. To obtain a sugar solution which will satisfy all requirements of the food laws and of buyers, it is recommendable to add small amounts of clacium hydroxide to the said ash-free, partially inverted, and preferably also concentrated sugar solution, until a pH of at least 8.5 is reached. Gelatin particles will then again precipitate and can be filtered out or removed by flotation. The sugar solution thus obtained, after another percolation through a weakly acid ion exchanger column to remove the calcium ions and adjust the pH, is colorless, fluid, ash-free, and satisfies all requirements both of the food laws and of consumers.

The mild acid cleaning of the juice can be combined with a known method of precipitation of the colloidal impurities with iron salts, especially iron(III) chloride. The pH value of 3.6 to 4.7 which is preferred in this case can be achieved by appropriate selection of the amount of the iron salt, and the juices are heated for about 15 minutes at 85° C with the iron salt added, and then they are centrifuged ("Zucker", 1954, 480).

The mild acid juice cleaning can, in like manner, be improved by flocculation with aluminum salts. For this purpose the flocculation is performed with sodium or ammonium alum solutions, preferably at a pH of 5.8 ("Zucker", 1954, 226).

It has surprisingly been found that the mild acid juice cleaning can be decidedly improved and that an easily filtrable juice can be obtained if the acidified raw juice is treated with traces of enzymes which cleave pectin. Such enzymes, chemically speaking, are especially pectinesterases, pectases and polygalacturosidases. Also suitable are intracellular enzymes, as well as enzymes fixed on supporting substances. Commercially available products which have proven usable for the purposes of the invention are PEKTINOL (Rohm & Haas), PANZYM KF (Boehringer), ULTRAZYM (Schubert KG) and ROHAMENT P (Rohm & Haas). The enzymes greatly differ in their activity. The amounts of pectin cleaving enzymes necessary for the achievement of the desired effect are extraordinarily small and, depending on the quality of the enzyme used, amount to approximately 1 to 100 ppm (mg/l) with respect to the amount of juice.

In the case of flocculation in the presence of pectin cleaving enzymes, it is preferably to operate at pH values and temperatures corresponding to their optimum action. It is a special advantage of this variant of the mild acid cleaning that a low acidification will suffice, namely pH values of as little as 4.5 to 4.7. For example, the optimum range of action for PEKTINOL is between pH 3.0 and 4.5. The optimum temperature is approximately 50° C. The length of treatment depends on the temperature, amounting as a rule to a few minutes. A part of the impurities separated in the presence of pectin cleaving enzymes is best returned to the process, because the flocculation is improved in this manner. This recycling can amount to up to 30% of the raw juice input.

In all of the above-described methods of the flocculation of pectin and protein components of the raw juice together with a small amount of cell fragments, the flocculated impurities are separated by known methods, especially by decantation, centrifugation and filtration. In the presence of pectin cleaving enzymes the separation achieved even by decantation is so complete that the clarifying layer can be followed down with a moving siphon. The siphoned juice is then passed through a separator or a filter press. In both cases it is clear pale yellow in color.

In practice it has also been found desirable to perform the flocculation by mild acid cleaning in accordance with the methods mentioned above, and to separate the flocculated impurities by flotation. This separation is accomplished when the flocculated, suspended particles attach themselves to finely divided gas bubbles in the solution and float to the surface. The gas bubbles can be produced by the expansion of physically dissolved gases, such as air or carbon dioxide, or by injecting some air or carbon dioxide ahead of the pump delivering the raw juice into the flotation vessel after the juice has been adjusted to the required temperature and injected with the required chemicals. The gases are then very finely divided by the pumps. In the flotation vessel the foam with the separated solid particles floats on the surface and is removed by the skimmer. The clarified juice is removed from the bottom. The flotations, too, are best followed by a fine filtration. The filtered juice is delivered to the ion exchanger station. Pulp, foam and the impurities are recycled to the classical works (tower or liming works).

Another method of mild juice cleaning, in which the glutamine and other amino acids as well as the invert sugar of the raw juice are preserved, but the colloids and protein substances which would harm the exchangers are removed, is liming or liming combined with carbonation. These operations, in a number of variants, are part of known juice purifying processes. For the purposes of the invention, the preliminary precipitation of the classical method of juice purification, for example, will suffice, in which the colloids and the insoluble calcium salts are precipitated by the addition of a relatively small amount of lime amounting to from 0.15 to 0.25%. In this process a pH of 10.8 to 11.2 is reached, depending on the acidity and buffering capacity of the raw juice. It is known that this flock is not filtrable economically on account of its glutinous nature and requires an additional filter aid, which will be the calcium carbonate formed in the main liming process of the classical method of juice purification. For the purposes of the invention it is sufficient to decant the flock from the preliminary separation and then centrifuge the separated juice (F. Schneider, "Technologie des Zuckers", 1968, pp. 261–310).

Another method of mild alkaline cleaning of juice is known as "separation saturation" (op. cit. p. 299), in which the lime and carbon dioxide are fed simultaneously while the pH value of the preliminary separation is maintained, i.e., from 10.8 to 11.2, with slight upward or downward variations. In the single-step separation saturation, the raw juice, lime and carbon dioxide react together simultaneously, at the optimum flocculation point of the raw juice, that is, at the end pH of the preliminary separation. Separation saturation can also be performed continuously by the Dorr method. Neither in the preliminary separation nor in the separation saturation is the invert sugar contained in the raw juice destroyed, i.e., the further processing is intentionally performed with thermolabile juices.

Still another method of mild alkaline cleaning of juices within the scope of the present invention is known as the Brunswick method, which is a stepwise separation saturation method in which the colloids are removed from the crude juice at lower pH levels than in the conventional separation saturation method. This method is characterized by outstanding ease in the settling and filtration of the sludge that is produced. For the purposes of the invention, separation saturation around pH 9, at which the raw juice colloids are flocked out and immediately enveloped by calcium carbonate, will suffice as the first step of the "simplified Brunswick" method of juice purification (op. cit., pp. 303–306). Lastly, mention will be made of the Sepa process (op. cit., p. 308), the first step of which will suffice. Just as a mild separation saturation which is a part of the above-mentioned, known juice purification methods can be the mild alkaline juice cleaning that is an important step in the process of the invention, so, too, the cleaned, decolloidized raw juice can be taken at the specified points from a sugar production process which includes one of the above-mentioned juice purification processes, and can be fed to the ion exchangers and further processed by the method of the invention to amino acids and conventional commercial sugar products.

The raw sugar beet juice mildly cleaned in the manner described is then passed through a cation exchanger in the $H^+$ form on which not only the inorganic cations but also the glutamine and asparagine and other amino acids which have been preserved unaltered in the mild cleaning process are retained, and they are thus removed from the juice. The purified juice can be delivered to the cation exchanger just as it comes from the acid or alkaline mild cleaning process, because the preliminary cleaning has made it easily capable of percolation and free of impurities that might clog or gum or otherwise irreversibly damage the ion exchangers. As it is known in connection with the complete desalting or raw sugar beet juice, pairs of ion exchangers are also used in the present case, and the juice is passed, preferably more than once, through strongly acid and then through weakly basic ion exchangers. It is furthermore known to combine deionization with a strongly acid ion exchanger for the production of sugar sirup with an inverting of the sugar. In the process of the invention, the ion exchange conditions are so interrelated that not only the valuable amino acids, the betaine and the organic acids can be obtained in a very simple manner, but also a fluid sugar or fluid raffinate is simultaneously obtained which fulfills all requirements. Fluid sugar and white invert sirup must comply with the "standards for fluid sugar and allied products from sugar beets or sugar cane." Accordingly, white invert sirup must not have more than 25 ICUMSA color units. Juices of this purity and colorlessness cannot be obtained by any of the known desalting processes.

Examples of strongly acid cation exchangers that can be used for the purposes of the invention are the resins AMBERLITE 200, AMBERLITE 252 (Rohm & Haas), LEWATIT SP 120 (Bayer), MONTECATINI C 300 AGRP, and C 300 P, or IMACTI C 12 or C 16 P. The resins AMBERLITE IRA 93 (Rohm & Haas) and LEWATIT MP 64 (Bayer) have proven useful as weakly basic ion exchangers. A strongly acid and a weakly basic ion exchanger are combined in each case into a single exchange unit. For continuous operation, two or more primary exchange units are provided, which are followed by at least one secondary exchange unit. The raw juice, after preliminary cleaning, flows through the first primary exchange unit and on through the secondary exchange unit until betaine begins to emerge from the first primary exchange unit. Then the feed is shifted to the available second or third primary exchange unit, and then the first primary exchange unit is purified and eluted or regenerated. The secondary exchange unit serves to capture the substances which are not retained by the cation exchanger of the primary exchange unit or which become re-eluted during the exchange. Since similar conditions can also occur on the anion exchanger, the secondary exchange unit also contains a weakly basic anion exchanger following the strongly acid cation exchanger.

Finally it is desirable for the final anion exchanger of the secondary exchange unit to be followed by still another small cation exchanger, for the purpose of neutralizing the possibly alkaline reaction of the solution emerging. A weakly acid exchanger will suffice as a rule. It depends on the composition of the raw juices and on the concentration of the individual substances they contain whether cation-anion-cation-anion-cation exchangers will be arranged in the manner described, or whether it will be more rational first to carry the juice successively through two or more cation exchangers (the "ring method", as it is called) and then through one or more anion exchangers, the secondary exchange unit and the final cation exchanger for neutralization. Although in the process of the invention those cation exchangers are selected as strongly acid cation exchangers which have an especially high capacity for betaine, the amino acids are displaced by the inorganic cations in the charging and the amino acids in turn displace the betaine, so that it is the betaine that first appears at the output of the cation exchanger of the primary exchange unit. The betaine is used in accordance with the invention as the lead substance, and a cation exchanger is replaced by a freshly regenerated cation exchanger or a freshly regenerated cation exchanger is hooked up as soon as betaine appears in the outrunning sugar solution. A primary exchange unit is thus replaced by a new one as soon as the betaine breaks through. Even small amounts of betaine can be reliably detected by known analytic methods, such as betaine periodide precipitation or precipitation with phosphotungstic acid. With betaine phosphotungstate precipitation, the occurrence of betaine in the outflow of the cation exchanger can be detected with photoelectric cells and thus the connection of the exchange units can be automated.

In accordance with the invention, therefore, one deliberately refrains from fully utilizing the charge capacity of the cation exchangers for amino acids. Since the betaine occurs in the outflow of the cation exchangers before the amino acids, a breakthrough of the amino acids into the juice can be reliably prevented and it can be kept free of amino acids by changing the cation exchangers upon the appearance of betaine. Up to this moment the outflow from the primary exchange unit is still virtually colorless and the secondary exchange unit that follows serves more for safety, so as to prevent ions and coloring substances from "slipping by." The difficulties so often described in the literature, which are encountered in the decolorizing of sugar juices after they have been purified with ion exchangers, have not been observed in the process of the invention; instead, the Maillard reaction, and the occurrence of color in the fluid sugar or fluid raffinate, are reliably prevented. The reason for this may lie in the method of operating the exchange units in the ion exchange, which has been described above, but probably the mild cleaning of the juice is also a contributing factor.

Without adversely affecting the production of the glutamine and the other amino acids, the rate of inversion and hence the composition of the fluid sugar which is simultaneously to be produced can be controlled by controlling the temperature of the raw juice during its treatment with the strongly acid cation exchangers. Both the cleaning of the juice and the percolation can be conducted so that inversion is virtually prevented and the cleaned raw juice contains only the fructose and glucose originating from the beet in an amount on the order of up to about 1% of the dry substance. In this case, the mild alkaline juice cleaning method, or the mild acid cleaning at the highest possible pH values, will be used, especially in the presence of pectin cleaving enzymes. The treatment in the strongly acid cation exchangers will then be performed at the lowest possible temperatures, especially below 15° C. Then the increase of the invert sugar during the exchanger treatment will remain minimal and will be less than 1%, as a rule, with respect to the dry substance. Under these conditions, therefore, not only glutamine and the amino acids are obtained, but also fluid raffinates, and these, if desired, are also cooked to sugar. This sugar qualifies as a raffinate with a color rating of 0 on the Brunswick point scale. The runoff is colorless and ash-free and is a fluid sugar of low inversion.

If a fluid sugar with a higher invert sugar content or invert sugar sirup is desired, higher rates of inversion can be allowed in the cleaning of the juice and the percolation. If the treatment with the ion exchangers is performed at higher temperatures, of, for example, 30° to 40° C, the saccharose can be cleaved largely to fructose and glucose without difficulty. After thickening, a fluid sugar sirup or invert sugar sirup will be obtained which will satisfy the most stringent requirements as regards color and ash content.

If the percolation is preceded by a mild acid juice cleaning operation, it may be desirable to clarify the deionized, partially inverted and preferably already thickened sugar solution with small amounts of calcium hydroxide. Depending on the quality of the juice, the amount of calcium hydroxide will be between 0.03 and 0.2% of the dry substance. This will bring the pH to more than 8.5. After clarification, the sugar solution is, of course, filtered. The excess calcium ions can be removed from the sugar solution by precipitation or cation exchange. Precipitation will be performed mainly with physiologically unobjectionable, inorganic acids which do not easily form soluble calcium salts, examples being oxalic acid, phosphoric acid and carbon dioxide. Weakly acid cation exchangers in the $H^+$ form are especially suited for the removal of excess calcium ions by ion exchange. Examples of suitable resins are IRC 50 and IRC 84 of Rohm & Haas, or LEWATIT CSP of Bayer.

In published attempts to produce amino acids and betaines in conjunction with the desalting of dilute juices, the glutamine contained in the raw juice is already broken down virtually completely, due to the classical method of juice purification, into pyrrolidonecarboxylic acid, which can only be captured on anion exchangers. Anion exchangers are substantially more expensive and have an appreciably lower capacity and shorter life than cation exchangers. On account of swelling and shrinkage in technical operation, they are more difficult to manage, and substantially larger amounts of water are needed to sweeten them than in the case of cation exchangers, i.e., the juice is more greatly diluted. Cation exchangers, however, are very stable and easy to elute and regenerate. For reasons of economy, therefore, it would be desirable for as much as possible of the non-sugar substances to be in a form in which they can be adsorbed by cation exchangers, that is to say, the acid amides, especially the glutamine and asparagine, should be preserved in their original form insofar as possible. This is assured by the mild juice cleaning of the invention, which precedes percolation through the ion exchangers. The betaine, the acid amides and the other amino acids are retained on the strongly acid cation exchanger, therefore, just as well as the inorganic cations K, Na, Ca and Mg which are to be removed in the course of the desalting. Since glutamine and glutamic acid amount quantitatively to about 50% of the amino acids present in the raw sugar beet juice, it signifies a considerable advantage that they can be obtained on the cation exchanger without decomposition. If a cation exchanger of the primary exchange unit is charged to such an extent that betaine occurs in the outrunning sugar solution and then, as described, one changes over to a freshly regenerated primary exchange unit or only to a regenerated strongly acid cation exchanger, the cation exchanger is sweetened by flushing it with one to two times the bed volume of deionized water. The sweetening solutions can best be carried also through a fresh primary exchange unit, but they can also be delivered into the secondary exchange unit. For the cutting out of the secondary exchange unit and its sweetening, the same is applicable as to the primary exchange unit. The cation exchanger can then be eluted in a known manner with solutions of other cations, especially ammonium ions. Which elutant is to be selected will depend on the form in which the amino acid is to be obtained. The use of an approximately 10% $Na_4OH$ solution for the elution has the advantage of high amino acid concentrations in the eluting solution. In the case of elution with ammonium ions and other cations, especially dilute NaOH, the cation exchanger must then, of course, be again regenerated, and this is done with dilute mineral acids.

Preferably, the cation exchanger is eluted with about 0.5 to 1.5N, and especially 1N hydrochloric acid, and is thereby simultaneously regenerated. One then obtained in the first runnings a fraction that is rich in glutamine, glutamic acid, pyrrolidonecarboxylic acid and hydrochloric acid. Upon concentration by evaporation, this mixture is converted to glutamic acid hydrochloride, which is insoluble in the excess hydrochloric acid and crystallizes out directly. In this case the regenerating agent expense is smaller, because elution with other cations, especially ammonium ions, is eliminated.

Surprisingly, the eluates of the cation exchanger in the process of the invention are not greatly discolored, apparently because of the use of the mildly cleaned raw juices, so that a direct crystallization of the pure amino acids or amides is possible. The case is much the same with the eluates from the anion exchangers. If the cation exchanger has been fractionally eluted with aqueous ammonium solution, glutamine is produced directly upon the concentration of the glutamine-rich fraction of the eluate. This glutamine is pure white after a single recrystallization. From other fractions, betaine and other amino acids can be obtained by crystallization according to known methods. If the ammoniacal or neutral eluate fractions cannot be processed to glutamine by an immediate and gentle process of concentration and they have to be stored for a period of time, or if they are heated for a short period, the glutamine becomes transformed to pyrrolidonecarboxylic acid. Now, if the eluates pretreated in this manner are again passed through a strongly acid ion exchanger, the pyrrolidonecarboxylic acid, as the only substance, will pass through the column as a colorless, aqueous solution. It can then be obtained colorless and pure by evaporation, or the aqueous solution can be transformed directly in a known manner, at little expense, to high purity glutamic acid, sodium glutamate or glutamic acid hydrochloride.

The weakly basic anion exchangers are regenerated in a known manner with ammonium hydroxide. The organic acids, especially citric acid, malic acid and oxalic acid, can then be obtained from the eluates. After the regeneration, the regeneration liquids are washed out and the regenerated exchangers are sweetened and reused.

The process of the invention is easily applicable to the production of amino acids from sugar cane juices, but in this case the composition of the amino acids is different. Asparagine is the main component rather than glutamine, amounting to about half of the amino acids present. Accordingly, sugar cane juices constitute an especially good source for the production of asparagine when processed by the method of the invention.

EXAMPLES

EXAMPLE 1

Raw sugar beet juice was acidified with hydrochloric acid to pH 3.3 and the colloids that coagulated were separated from the juice in a beaker centrifuge. This juice was then passed through a column containing a strongly acid cation exchanger (SP 120) and then through a column containing a weakly basic anion exchanger (LEWATIT MP 64). The juice leaving the cation exchanger had a temperature of 26° C. The product was a virtually ash-free, odorless, partially inverted sugar solution of about 12° Brix. After vacuum concentration to about 65° Brix it had a slightly greenish tinge and its viscosity was somewhat higher than that of commercial fluid sugar. This sugar solution was adjusted to pH 9.5 to 10 by the addition of a small amount of calcium hydroxide. After a brief period gelatin particles separated which could be removed by filtration. The filtered sugar solution was percolated through a weakly acid cation exchanger (LEWATIT CSP). The sugar solution thus treated was colorless and odorless, as fluid as normal fluid sugar, and ash-free. The pH was about 4.5. Analysis on a chromatographic column gave the following composition:

| | | |
|---|---|---|
| Oligosaccharides | 0.07% | of total solids |
| Saccharose | 59.3% | of total solids |
| Glucose | 20.9% | of the dry substance |
| Fructose | 19.7% | of the dry substance |
| Raffinose | 0.23% | of the dry substance |
| | 100.2% | |

EXAMPLE 2

Raw juice with a glutamine content of 1.8% and a free glutamic acid content of 0.08% with respect to dry substance, was acidified at 40° C with hydrochloric acid to pH 4.2, and treated with 0.001% pectinase (Pektinol of Rohm & Haas). The settling layer was followed down with a movable siphon, and the liquid siphoned out, which contained only a few flocks in suspension, was filtered through a pressure filter. The clear solution was subjected to automatic amino acid analysis (Beckman Multichrom):

Glutamine 1.73% of the dry substance
Glutamic acid 0.08% of the dry substance 50 liters of the raw juice thus pretreated were passed through five columns, three of which were packed with 2 liters each of strongly acid exchanger resin (Montecatini C 300 AGRP) and two with 2.5 liters each of weakly basic exchanger resin (MP 64). The columns were washed with water in the usual manner. The total liquid output from Column 5 was concentrated. The product was a clear and colorless sugar solution of excellent flavor having a 2.17% inversion:

Ash content: 0.008% of the dry substance
Icumsa color units: 3.0

Then the columns were eluted individually with ammonia. The glutamine and betaine content in the individual fractions of the eluate was determined, and amounted to the following percentages of the glutamine and betaine originally contained in the 50 liters of raw juice:

Eluate of Column I: glutamine 0%, betaine 1%
Eluate of Column II: glutamine 85%, betaine 31%
Eluate of Column III: glutamine 15%, betaine 68%.

The eluate from Column II was concentrated in vacuo to approximately 500 ml. 23 g of crystals formed, of which 60% consisted of glutamine (the remaining 40% was composed largely of tyrosine).

The filtrate of the above precipitate was further concentrated in vacuo to about 380 ml and seeded with glutamine. Yellowish-brown crystals precipitated overnight and weighed, after washing and vacuum drying, 52.6 grams. They consisted to more than 90% of glutamine. After a single recrystallization in the conventional manner with the addition of animal charcoal, 45 g of pure white crystals were obtained with a melting point of 184° C and a rotation of $[\alpha]_D^{23} + 6.0°$ (c = 3.6 in water).

EXAMPLE 3

Raw juice with a glutamine content of 1.8% and 0.08% of free glutamic acid with respect to dry substance was acidified at 45° C with hydrochloric acid to pH 4.2, treated with 0.001% pectinase (Pektinol of Rohm & Haas) and clarified with a Westfalia separator.

2000 liters of this juice were cooled down to room temperature and passed through 10 exchanger columns. The exchangers were connected in the series: A1 - B1 - A2 - A3 - A4 - A5 - B2 - B3 - B4 - B5 (A = acid exchanger resin, B = basic exchanger resin). A1, A2, A3 and A4 contained each 50 ml of Amberlite 200 and A5 contained 50 liters of Amberlite 252.

All of the basic exchangers were filled with 50 liters each of IRA 93. After the betaine broke through in the outflow from A4, the juice percolation was stopped and the whole series of columns was washed with water.

All of the liquid from the final basic column was concentrated in vacuo down to a dry substance content of 65%. 99% of the sugar originally present was obtained in the form of a purely sweet tasting sugar solution containing 7.17% invert sugar with respect to dry substance.

Ash content: 0.008% of dry substance
Icumsa color units: 7.9

All ten columns were then eluted with 4% ammonia. The glutamine was found mainly on A4, the betaine mainly on A5. On column A3, neutral and basic amino acids, especially γ-aminobutyric acid, were retained in addition to potassium, sodium, calcium, magnesium etc., amounting to virtually 100% of the input of A1 and A2. The eluate from A4 had a total glutamic acid content (glutamine + pyrrolidonecarboxylic acid + glutamic acid) of 3.38%.

One liter of this eluate was concentrated in vacuo to a thick sirupy consistency, the concentrate was dissolved in 100 ml of 30% hydrochloric acid, and was refluxed at 95° to 100° C.

After cooling, the precipitated crystals were filtered out and washed with a small amount of 25% hydrochloric acid. After vacuum drying at 30° C they proved to be already virtually pure glutamic acid hydrochloride:

46 g$[\alpha]_D^{20} + 25.1°$ (c = 6 in 1N HCl)

Upon one recrystallization from a little water:

$[\alpha]_D^{20} + 24.7°$ (c = 6 in 1N HCl), M.P. 212° C (decomp.)

After standing for 5 months, another specimen of the eluate from A4 was processed as follows: 200 ml was heated overnight at 90° C, cooled and passed through a strongly acid ion exchanger, and washed with water.

Upon the concentration of the percolated liquid, 6.5 g of flask residue was obtained, which was nearly pure pyrrolidonecarboxylic acid $[\alpha]_D^{20} - 10.2$ (c = 6 in water).

After a single recrystallization from water the substance was pure:

M.P. 162°-163° C $[\alpha]_D^{20} - 11.6$ (c = 6 in water).

The eluates from the five basic columns had the following composition:

| | B1 | B2 | B3 | B4 | B5 |
|---|---|---|---|---|---|
| Sulfate % of dry subst. | 13.8 | 0.5 | 0.3 | 0.2 | 0.1 |
| Chloride % of dry subst. | 11.8 | 37.8 | 23.3 | 0.5 | 0.5 |
| Phosphate % of dry subst. | 1.4 | 1.6 | 13.1 | 35.8 | 0.1 |
| Mixed organic acids % of dry subst. | 73.0 | 60.1 | 63.2 | 63.5 | 99.3 |

EXAMPLE 4

Raw juice with a glutamine content of 1.8% and 0.08% of free glutamic acid was subjected to a combination liming and carbonation under the following conditions:

Total lime: 0.5% with respect to the juice
Alkalinity of saturated juice: 0.05% CaO
pH of saturated juice: 9.7
Temperature: 75° C The hot-filtered juice was cooled and subjected to automatic amino acid determination:

Glutamine: 1.65% of the dry substance
Glutamic acid: 0.10% of the dry substance

The juice thus pretreated, having a temperature of 18° C, was passed through a series of four ion exchangers, of which 1 and 3 were provided with a strongly acid exchange resin (Amberlite 200) and 2 and 4 with weakly basic resin (IRA 93). When betaine broke through from column 1, the percolation was stopped and columns 3 and 4 were "sweetened". The total liquid from column 4 was concentrated, and yielded a colorless, clear sugar solution of perfect flavor. The invert content was 1.79% of the dry substance.

Ash content: 0.015% of the dry substance
Icumsa color units: 6.2.

EXAMPLE 5

Raw juice which had passed through the regular manufacturing procedure was tapped from the end of the second third of a Brieghel-Muller preliminary separator. It had a pH of 10.3 and an alkalinity of 0.075% CaO. The temperature was 53° C. The juice, which had been well flocculated under these conditions, was tested after fine filtration for its glutamine and glutamic acid content:

Glutamine: 1.40% of the dry substance

Glutamic acid: 0.08% of the dry substance.

The juice thus pretreated was again percolated through ion exchangers (arrangement and procedure as in Example 4). The liquid from the 4th column was concentrated. The product was a purely sweet, colorless, clear sugar solution having an invert sugar content of 4.45% with respect to dry substance.

Ash content: 0.004% of the dry substance

Icumsa color units: 8.9

EXAMPLE 6

Raw juice with a glutamine content of 1.8% and 0.08% free glutamic acid was put through the following purification steps:

1. Preliminary separation by the Brieghel-Muller process at 53° C and a final alkalinity of 0.265% CaO
2. Main separation with 1.1% CaO at 88° C.
3. First carbonation with stirring at 88° C to pH 10.0 at 0.075% CaO alkalinity.

This carbonated juice was directly filtered, cooled and analyzed:

Glutamine: 0.83% of the dry substance

Glutamic acid: 0.17% of the dry substance

The liquid was percolated using the arrangement and procedure described in Example 4. The liquid from the last column was thickened and a perfect-tasting sugar solution was obtained, which was 1.46% inverted.

Ash content: 0.020% of the dry substance

Icumsa color units: 13.2.

It will be appreciated that the instant specification and examples are set forth by way of illustration and not limitation, and that various modifications and changes may be made without departing from the spirit and scope of the present invention.

What is claimed is:

1. A process for the separation of amino acids from raw sugar juice containing impurities and amino acids, comprising coagulating the impurities in said juice, separating the juice from the coagulated impurities, passing the juice successively through an acidic cation exchanger and a basic anion exchanger thereby to adsorb the dissolved amino acids, eluting the ion exchangers with an ionic solution thereby to release the adsorbed amino acids, and collecting an amino acid-rich eluate.

2. The process of claim 1, wherein the amino acid-rich eluate is collected as a plurality of fractions each having a different amino acid content.

3. The process of claim 2, wherein one of said fractions is rich in glutamine or glutamic acid hydrochloride, and said one fraction is concentrated thereby to crystallize said glutamine or glutamic acid hydrochloride.

4. The process of claim 1, wherein a pectin-cleaving enzyme is added to the juice prior to its passage through the ion exchangers.

5. The process of claim 1, wherein the coagulation of impurities is effected by acidifying to a pH of about 2 to 5, and the coagulated impurities are separated from the juice by flotation.

6. The process of claim 1, wherein at least two cation exchangers are employed in parallel, flow of juice through one being discontinued and shifted to another before the capacity of the first cation exchanger to adsorb amino acids has been fully utilized but when betaine is present in the sugar solution flowing out of said first cation exchanger.

7. The process of claim 1, wherein the basic ion exchanger is weakly basic and is eluted with a solution of ammonium hydroxide, the eluate being collected in fractions of which one is rich in organic acids, the organic acid-rich fraction being treated to recover citric acid, malic acid and oxalic acid therefrom.

8. The process of claim 1, wherein the juice is passed through a plurality of strong cation exchangers and a plurality of weak anion exchangers.

9. The process of claim 1, wherein the solution is passed through the ion exchangers at a temperature below about 15° C and water is removed from the fluid raffinate by evaporation under vacuum, thereby to effect crystallization of the sugar.

10. The process of claim 1, wherein the coagulation of impurities is effected by acidifying to a pH of about 2 to 5, including the further steps of adding calcium hydroxide to the sugar solution which has passed through the cation and anion exchangers, and then contacting said solution with a weak cation exchanger or with an acid which forms water-insoluble calcium salts, thereby to reduce the calcium content to predetermined level.

11. The process of claim 1, wherein the coagulation of impurities is effected by adding lime to the juice to produce a pH of about 11.

12. The process of claim 11, wherein carbon dioxide is added along with the lime.

13. The process of claim 4, wherein the coagulation of impurities is effected by acidifying to a pH of about 2 to 5, the juice is thereafter passed through a plurality of weak anion exchangers and a plurality of strong cation exchangers, at least two of the cation exchangers being in parallel with one another and at least two being in series with one another, flow of juice through one of the parallel cation exchangers being discontinued and shifted to another before the capacity of the first cation exchanger to adsorb amino acids has been fully utilized but when betaine is present in the sugar solution flowing out of said first cation exchanger, elution of said cation exchangers being effected with a solution containing ammonium ions.

* * * * *